United States Patent [19]

Pozin et al.

[11] 4,290,299
[45] Sep. 22, 1981

[54] APPARATUS FOR CONTINUOUS TEMPERATURE MEASUREMENT OF THE DEW POINT OF FLUE GASES

[76] Inventors: Mikhail A. Pozin, 2960 Lake St., Apt. 143, Lake Charles, La. 70601; Mikhail B. Serkh, Posledny Per 15, Apt. 30, Moscow 10392, U.S.S.R.

[21] Appl. No.: 904,603

[22] Filed: May 10, 1978

[51] Int. Cl.² .......................................... G01N 25/02
[52] U.S. Cl. .................................................. 73/17 A
[58] Field of Search ................................ 73/17 A, 29

[56] References Cited

U.S. PATENT DOCUMENTS 3,780,564  12/1973  Levina et al. ................... 73/17 A
3,930,398   1/1976  Levina et al. ................... 73/17 A Primary Examiner—S. Clement Swisher
Attorney, Agent, or Firm—Gunn, Lee & Jackson

[57] ABSTRACT

A dew point temperature monitor for use in a flue gas stream is disclosed. It incorporates means for sensing the presence of condensate formed on a transmitter having an exposed surface in the flue gases, a thermocouple for measuring the temperature on the surface of the transmitter and a feedback loop for controlling operation of a heating and cooling system to vary the temperature of the transmitter to thereby vary the rate at which condensate is accumulated. The control apparatus includes control means for the control of the heater which is an electrical heater. The cooling system utilizes a flowing coolant fluid delivered through a suitable valved distribution system. They are manipulated by the measurements obtained by the sensors on the surface of the transmitter. The apparatus measures and records dew point temperature.

19 Claims, 12 Drawing Figures

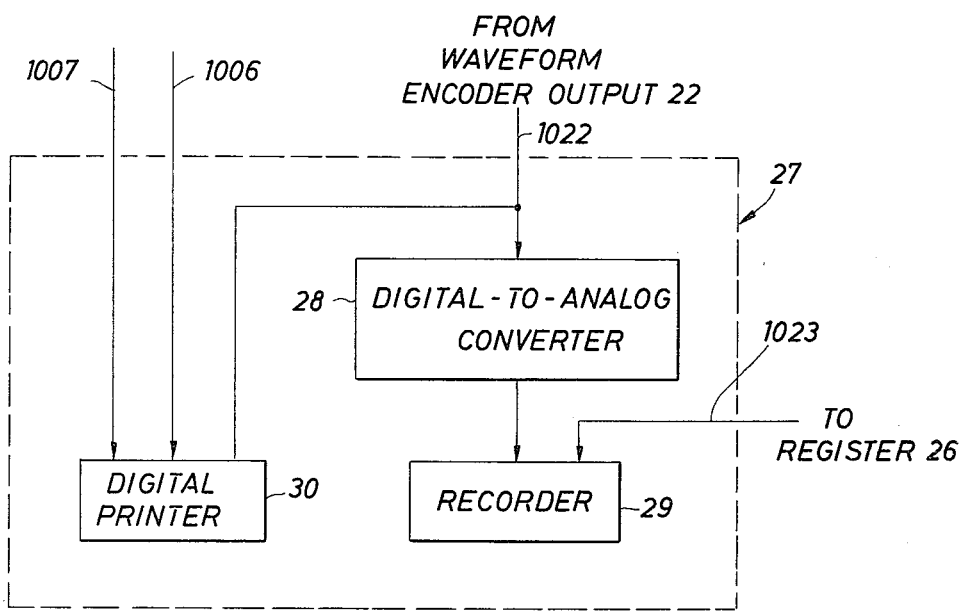
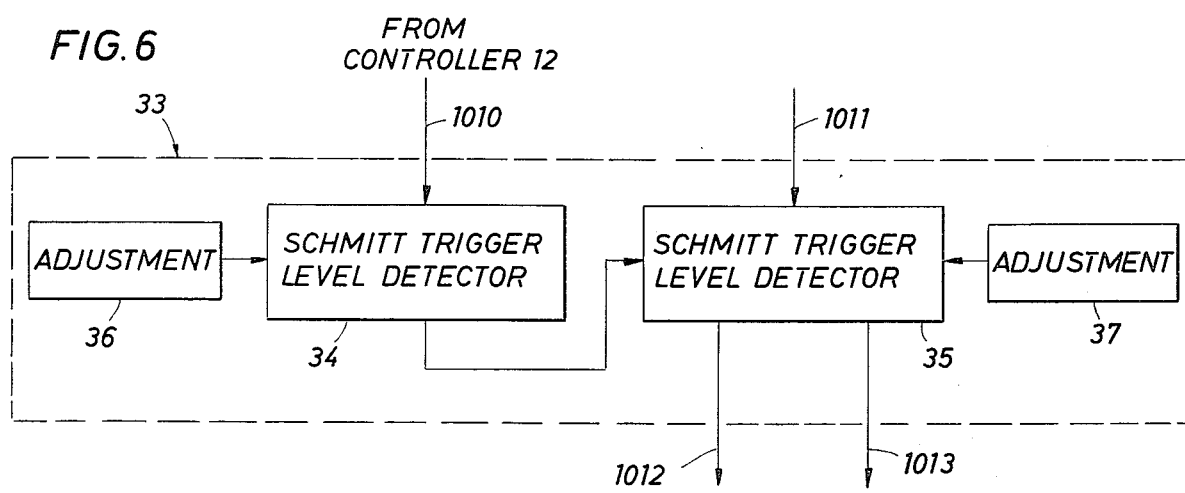
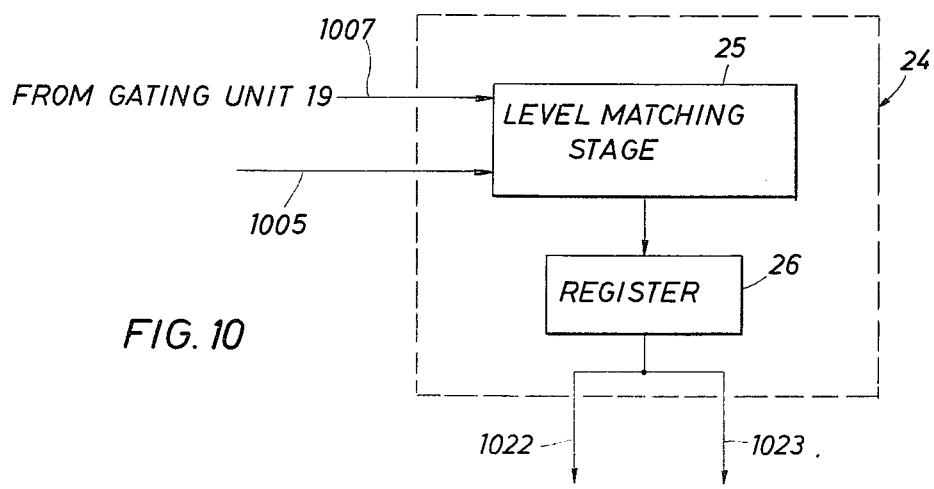

APPARATUS FOR CONTINUOUS TEMPERATURE MEASUREMENT OF THE DEW POINT OF FLUE GASES

BACKGROUND OF THE DISCLOSURE

The present invention relates to a measuring device and, more particularly, a measuring device which continuously measures the temperature corresponding to the dew point of flue gases. This device is related to the apparatus described in previously issued U.S. Pat. No. 3,930,398, dated Jan. 6, 1976. In that apparatus, a signal representative of the dew point controls certain heating and cooling apparatus dependent on the formation of a thin condensate film from the flue gases. In that apparatus, the signal is applied through various electronic equipment to control a heating element and a coolant flow valving system. Between the heating element and the cooling apparatus, the rate at which condensation forms on the surface is controlled. It further insures control of the temperature of the surface which is exposed to the flue gases. It can manipulate this surface temperature upwardly or downwardly as required.

All values of temperature of the condensing surface exposed to the flue gases are received by the temperature recorder for continuous monitoring and manipulation of these values. This continuous signal enables continuous measurement of the dew point temperature with a useful level of accuracy and with minimum fluctuations when the dew point temperature approaches near the temperature of the condensation surface. There are, however, limitations on the operation of the disclosed apparatus.

One limitation on the apparatus of the above discussed patent occurs if the dew point temperature is lower than the temperature of the condensation surface. At this point in time, the surface is too hot to permit condensation, and, accordingly, the apparatus does not form a signal indicative of dew point temperature. It is known that it is somewhat lower, but it is impossible to know how much lower the actual dew point temperature is.

Conversely, when the temperature of the flue gases flowing past the condensation surface is considerably higher than the dew point temperature, then the dew point temperature of the flue gases is difficult to measure because of the great gap. In other words, the large differential temperature makes it difficult to obtain a correct measure of the dew point temperature, and, with this difficulty, there is difficulty in correctly controlling application of the heating and cooling means.

The apparatus of the above mentioned patent is capable of tracking the dew point temperature of the flue gases within certain accuracy limits. These accuracy limits are unduly broad or wide, and, accordingly, the present invention is able to track the dew point temperature variations and fluctuations with much greater accuracy.

The present invention is, by contrast, a more accurate device for providing continuous control of dew point temperature measurements. Moreover, it is able to provide dew point temperature measurements over a wider range of fluctuations, thereby permitting it to be used in different situations. The dew point temperature of flue gases is, in part, dependent on many variables, including proximity to the furnace, the feed stock for the furnace, the presence or absence of sulfur in the coal in the furnace, heat exchangers in the stack, pollution control devices in the stack and so on. It will be understood that the above mentioned factors and other factors may cause the dew point temperature to fluctuate over an extremely wide range. In some instances, it may be quite low, while in other instances the normal operating dew point temperature will be comparatively high. Use of the present invention prolongs the life of large and expensive boilers and boiler related equipment. This is particularly true where the boiler is stoked with high sulfur fuels. High sulfur fuels present severe pollution control problems in that the sulfur cannot be permitted to escape to the atmosphere because it takes the form of various sulfur oxides. Sulfur oxides are considered detrimental to the environment and, therefore, require rigorous pollution control measures. The present invention cooperates with such controls and, more importantly, enables the life of large, expensive boiler installations to be materially extended.

This device utilizes an exposed condensation surface in the flue. The flue gases are conducted past the surface. By control or manipulation of the surface temperature, a thin film of condensate is formed on the surface. The present invention measures the point at which the condensate film is formed from the vaporized gases in the flue.

BRIEF SUMMARY OF THE DISCLOSED APPARATUS

This apparatus incorporates an exposed condensation collection surface. This surface is exposed to flue gases of interest, and, in conjunction with heating and cooling means below the surface, its temperature is manipulated so that a thin film condenses from vapors in the flue gas. The temperature of the surface at which this is formed is related to the dew point temperature. The surface is immediately adjacent to a heating element and a cooling element on the underside. The condensation surface is temperature measured, and this signal is transferred to a memory unit. The memory unit incorporates a storage register. The storage register stores a value representative of dew point temperature. The memory unit further stores additional control signals. As an example, it is necessary to cool or heat the surface. The memory unit also stores the cooling speed control signal. It stores the last set of values and the change or direction of the values. By storage of the last values, the apparatus is able to achieve a highly accurate measure of dew point temperature and, thereby, broadens the operating temperature range of the present apparatus.

BRIEF DESCRIPTION OF THE DRAWINGS

FIG. 4 is a schematic block diagram of the dew point temperature data register unit;

FIG. 6 is a schematic block diagram of the cooling speed control unit;

FIG. 10 is a block diagram of the memory unit;

DETAILED DESCRIPTION OF THE ILLUSTRATED APPARATUS

Figure 1:
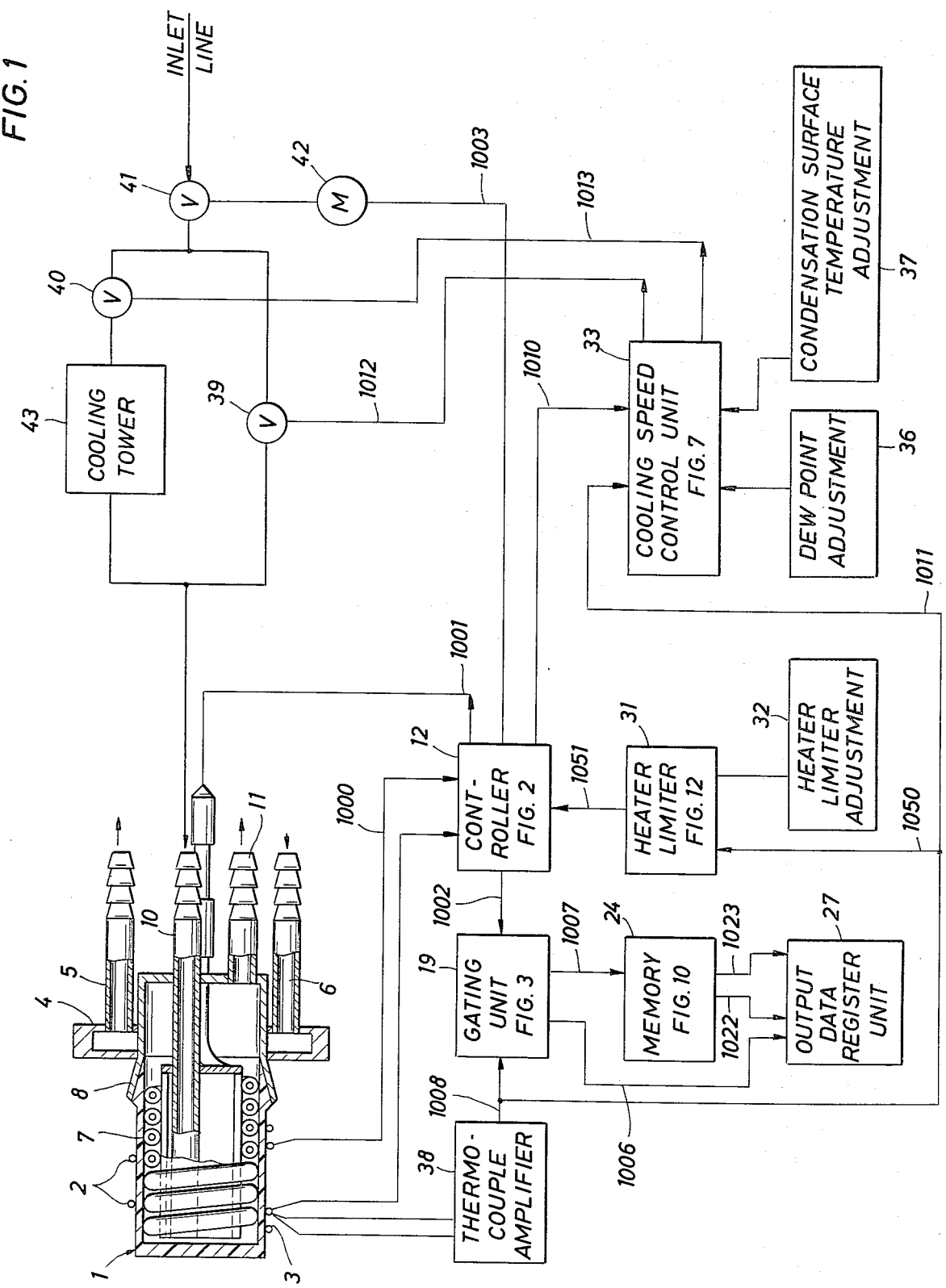
FIG. 1 is a view, partly an electrical schematic and partly mechanical layout, which shows the present invention and particularly illustrates the control system in schematic fashion.

Attention of the reader is first directed to FIG. 1 of the drawings. In FIG. 1 of the drawings, a transmitter 1 is illustrated in sectional view. The apparatus of FIG. 1 is a dew point transmitter. It includes a cylindrical shell formed of material which is an electrical insulating material. In addition, it is a heat resistant material. A portion of the external surface of the cylinder is used for condensation of vapors in the flue gases which flow past it.

It will be understood that the present apparatus is installed at a convenient location in the chimney or flue of a large industrial boiler installation. The precise placement is preferably sufficiently remote from the boiler so that it is exposed to the uprising flue gases. It is preferably not placed at the very tip of the flue or chimney; rather, it is placed closer to the boiler, itself. Because boiler installations vary widely, the precise location is varied over a wide range of intermediate locations between the boiler and the chimney exit.

The external surface of the cooling transmitter 1 is exposed to flue gases. Flue gases condense on this surface, dependent on a number of scale factors including temperature of the gas, amount of water and other condensable fluids in the gas, and so on. These gases are detected by exposed external electrodes 2, as will be described. The electrodes 2 are spaced electrical conductors. Conduction between them is water dependent. A thermocouple 3 is also supported on the surface. Indeed, if desired, multiple electrical terminals 2 and thermocouples 3 can be spaced about the exterior of the temperature transmitter. Further, the externally exposed transmitter surface is thermally connected to a first or auxiliary cooling system 4. The cooling system 4 incorporates a jacket which surrounds the one end of apparatus to deliver coolant to the heated surface 1 for reducing its temperature in a controllable fashion. More will be noted concerning this hereinafter.

The auxiliary cooling system incorporates a discharge pipe 5. The discharge pipe 5 cooperates with an inlet pipe 6 to deliver a liquid coolant which flows in an encircling pattern within the surrounding flange-like structure of the device to at least partly cool a portion of the device.

The numeral 7 identifies an electric heating element which is wrapped into a multiturn coil or spiral. This extends along the interior of the cylindrically shaped housing 1. The coils 7 are snugly fitted against the cylindrically shaped, external cover 1. That is to say, they contact the inner face of the device. The coils are arranged in a spiral or helix on the interior. They serve as a guide for fluid flow for a second cooling system. The second cooling system includes an inlet pipe 10 which extends to the very end of the cylinder 1 and an outlet pipe 11. Coolant introduced through the inlet 10 is delivered to the very end and is funneled in spiral flow patterns back out to the chamber connected to the pipe 11. The pipe 11 removes the heated coolant.

It will be observed that there are two cooling systems, the first one including the pipes 5 and 6 and the second one including the pipes 10 and 11. The first cooling system has a fixed flow rate. The second cooling system is adjustable in accordance with the teachings of the present invention. The flow rate is varied in a manner to be described. Accordingly, the cooling system, including the inlet 10 and the outlet 11, opens down to the very center of the container 10. The first cooling system cools to the flange which mounts the equipment. The first cooling system can be omitted in low temperature applications; it is preferably kept in the equipment to cover wide range temperature fluctuations and, more particularly, to protect the equipment in extremely high temperature installations from heat transfer through the wall which mounts the device in the flue gas flow.

The coolant which is used is either gas or liquid. The choice of gas or liquid, the specific heat thereof, the flow rate, the size of the pipes, the pressure drop in the cooling system and other factors of this sort are all scale factors which can be varied depending on the severity of the installation.

The reader's attention is next directed to a temperature controller 12 in FIG. 1. The input to the controller 12 is obtained from the electrodes 2. The electrodes 2 are on the external exposed condensing surface of the transmitter unit 1. The surface is a condensation surface. It functions in the manner of placing a cool, metal surface in a room laden with warm, moist air. The cool surface will condense water out of the air provided the dew point temperature of the water exceeds the temperature of the surface. The temperature controller 12 utilizes a voltage amplifier shown in FIG. 2 which forms an output signal. As shown in greater detail in the block diagram schematic of FIG. 2, the controller 12 incorporates a power amplifier 14. The amplifier 14 is connected to two devices. It is connected to a heating element regulator 15 and a cooling element regulator 17. It will further be observed in FIG. 2 of the drawings that the power amplifier 14 receives its input signal through a preamplifier 13. The preamplifier is an empedence matching device which provides some signal boost. In addition, FIG. 2 discloses heating and cooling element regulator circuit setpoint means 16 and 18 which provide control signals for the heating and cooling element regulators in a manner to be described hereinafter.

Figure 2:
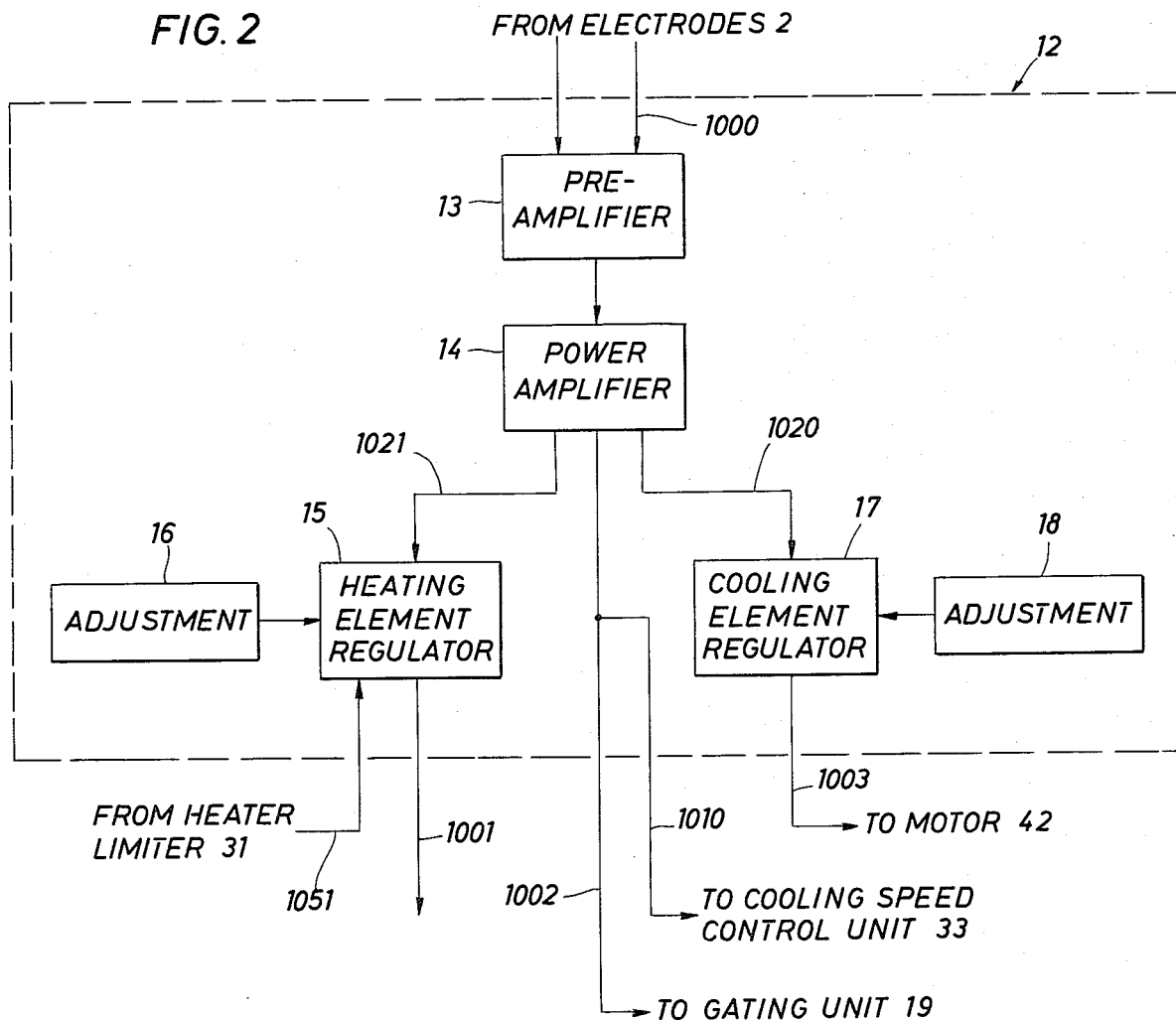
FIG. 2 is a block diagram schematic of the temperature control unit of the transmitter condensation surface.
Figure 3:
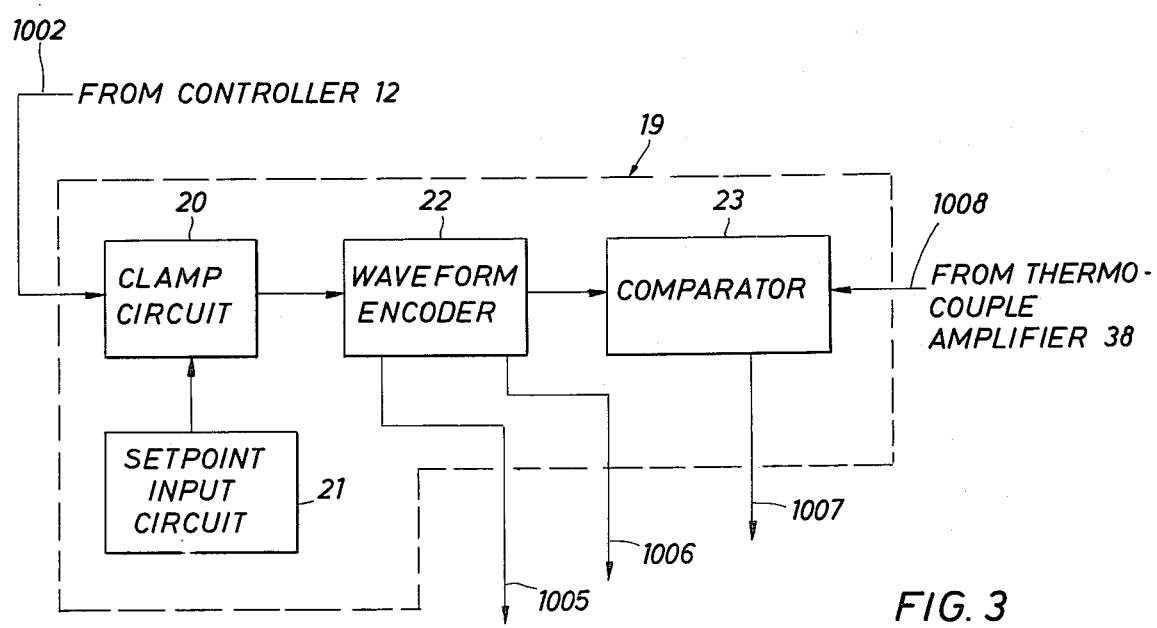
FIG. 3 is a schematic block diagram of a gating circuit.

In FIG. 2, the power amplifier 14 has three outputs, two of which have been discussed. The third output is to the gating unit 19. This is shown in FIG. 3. In FIG. 3, the gating unit is shown in greater detail. The gating unit 19 selects the values of the dew point temperature out of all values obtained from the surface of the temperature condensation apparatus shown in FIG. 1. It incorporates a dew point clamp circuit 20. The clamp circuit 20 operates in conjunction with a setpoint circuit 21. The setpoint circuit 21 serves as a control means for the clamp circuit 20. The signal from the power amplifier passes through the clamp circuit 20 which limits its excursion and then is input to a time-dependent linear-decay waveform circuit 22. This signal is encoded in the waveform output of the encoder 22. The output signal of the encoder 22 is then supplied to a comparator 23. The comparator circuit receives an input from a thermocouple amplifier 38 which will be described. It compares the two signals and forms an output indicative of the comparison of the two including relative polarity and magnitude of the difference.

The outputs of the gating unit are obtained from the comparator 23 and the waveform encoder 22.

In FIG. 10 of the drawings, a memory unit 24 is illustrated. The memory unit 24 recalls or remembers values representative of the dew point temperature selected by the gating unit. The input of the memory 24 is connected with the output of the gating unit 19 shown in FIG. 3. It incorporates a level matching stage 25, a voltage level control circuit. The storage register 26 is capable of storing in digital word form the signals which are input to it.

FIG. 4 of the drawings discloses an output data register unit 27. It is a device for registering or recording operation of the entire apparatus and, in particular, forming a dew point temperature record. It can be formed of any suitable components, including digital or analog storage devices. In the illustrated embodiment, the output data register unit 27 is shown to incorporate a digital-to-analog convertor 28. It is connected to the memory unit 24 (see FIG. 10), and the output of the convertor 28 is, in turn, connected to a recorder 29. The recorder 29 is any type of device which forms a permanent or temporary record. In addition, the numeral 30 identifies a digital printer which is connected to the input signal. It forms an alternate printout.

Returning now to FIG. 1 of the drawings, it will be observed that the device utilizes a dual cooling system. This was mentioned earlier where the conduit pairs were identified to include the conduits 5 and 6 which deliver a fixed rate of flow to the outer flanged assembly. A second coolant is delivered through the inlet 10 and is removed through the outlet 11. This cooling system is connected with more complex apparatus. This cooling system includes an inlet line connected to a first control valve 41 which, in turn, is opened or closed by a motor 42. When the valve is open, it permits the flow of cooling fluid to the system. The system further branches into a pair of parallel conduits input to the inlet 10. One branch is controlled by the valve 39. The second branch is independently controlled by the valve 40. The valves 39 and 40 are provided with setting controls which open the valves by a specified amount. The numberal 43 identifies a cooling tower. The cooling tower is incorporated to achieve even greater temperature drop on the cooling fluid supplied through the line 10.

With the foregoing in mind, the apparatus functions to provide controlling signals for the various valves so that they can be opened and closed in the proper amount to achieve the necessary amount of cooling. To this end, the description of the electrical components which control these valves will continue.

The apparatus incorporates a thermocouple amplifier 38 shown in FIG. 1 of the drawings. It forms an output signal which is supplied to a cooling speed control unit 33. The cooling speed control unit 33, when supplied with the thermocouple signal and a signal from the controller 12, manipulates the valves 39 and 40. It is additionally supplied with a signal from a dew point temperature selection circuit 36 and a second selection circuit 37 which provides a signal representative of the desired condensation surface temperature. This is more aptly shown in FIG. 6. There, the cooling speed control unit 33 incorporates the illustrated components in block diagram form. The cooling speed control unit 33 is constructed and arranged with the selection circuits 36 and 37 controllably adjusting operation of the circuits 34 and 35. They are, in turn, amplifier circuits which have a relay actuated transient response control feature for the cooling systems. Because there are two control valves 39 and 40, they can be set differently. Thus, the two valves are controlled separately so that they can be brought on line at different times. This is particularly advantageous when wide, dynamic operational range is considered necessary.

Figure 12:
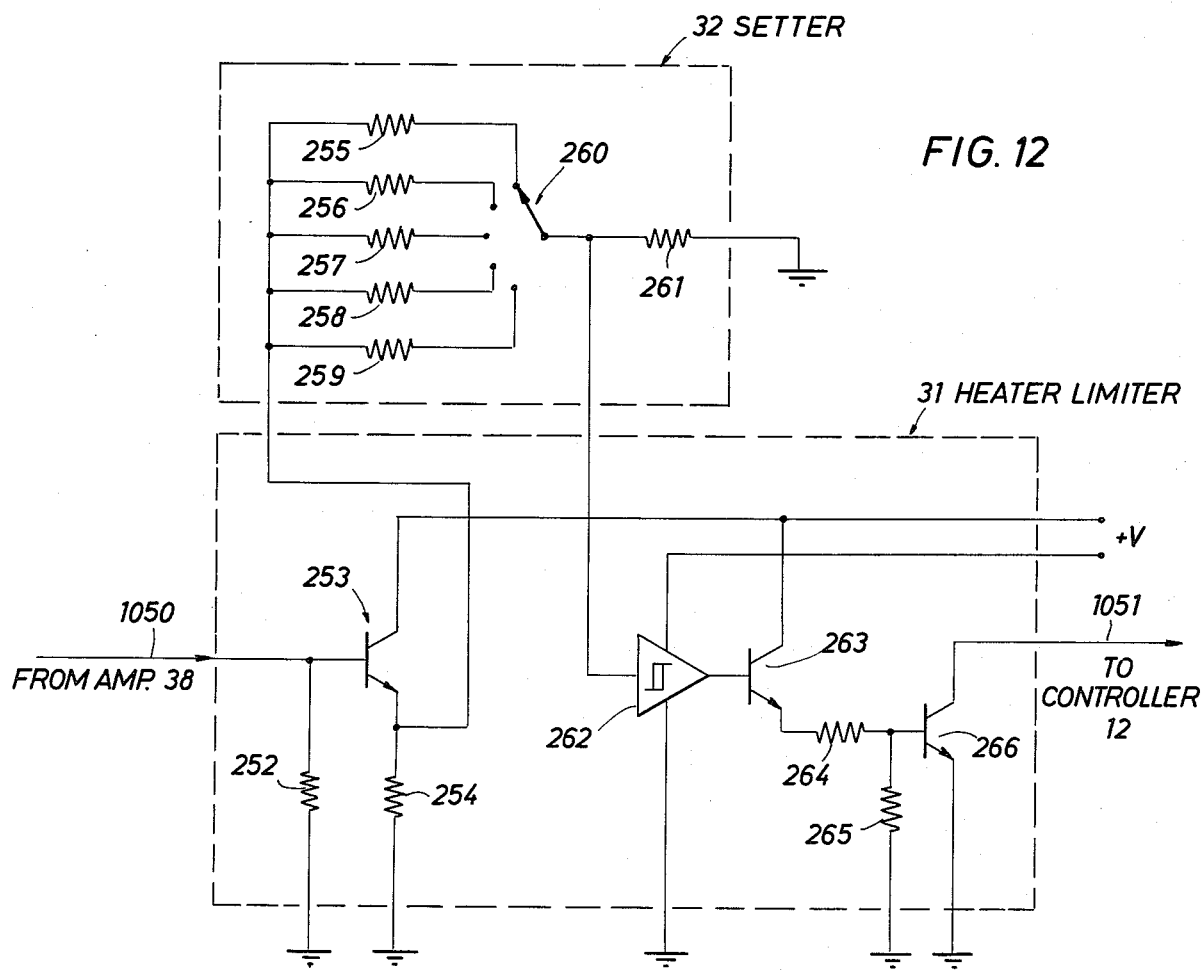
FIG. 12 is an electrical diagram of the heating control circuit.

Attention is next directed to FIG. 12 of the drawings. FIG. 12 of the drawings shows a circuit which limits the controlled heating device 7 on the interior of the condensation surface 1. The heater limiter 31 is shown in detail in FIG. 12. It is manipulated by a selector 32. Accordingly, the selector 32 is operated to a desired level, and the heating limiter then is triggered into operation to thereby controllably permit the heater to be energized but within specified limits. The net result is that heating is achieved, but preset limits are not exceeded.

Operation of the system can now be better understood. The system operates in the following manner. As moisture of any type condenses on the outer surface, the presence of condensation is determined by the electrodes 2 mentioned above. This is additionally reflected by changes in the temperature of the surface which is sensed by the thermocouple 3. The thermocouple 3 provides an input signal to the thermocouple amplifier 38. This, in turn, forms a signal which is provided to the circuitry shown in FIG. 3 whereby the range of variations is clamped, and it is converted into a modified waveform supplied to a controller circuit 12. The controller circuit 12 (see FIG. 2) includes suitable amplification whereupon the amplified signal is then utilized to control heating and cooling element regulators 15 and 17. The regulators 15 and 17 then control the application of electrical power to the coil 7 (for heating purposes) or an increased coolant flow through the conduits 10 and 11 (through manipulation of the valves 39, 40 and 41 which are upstream). It is primarily this cycle of operation which is of interest in the remaining description. This sequence of operation is modified by several factors, such as limitations on the swing of the current applied to the electrical heater 7. This will be better understood on a more detailed review of the drawings.

Figure 5:
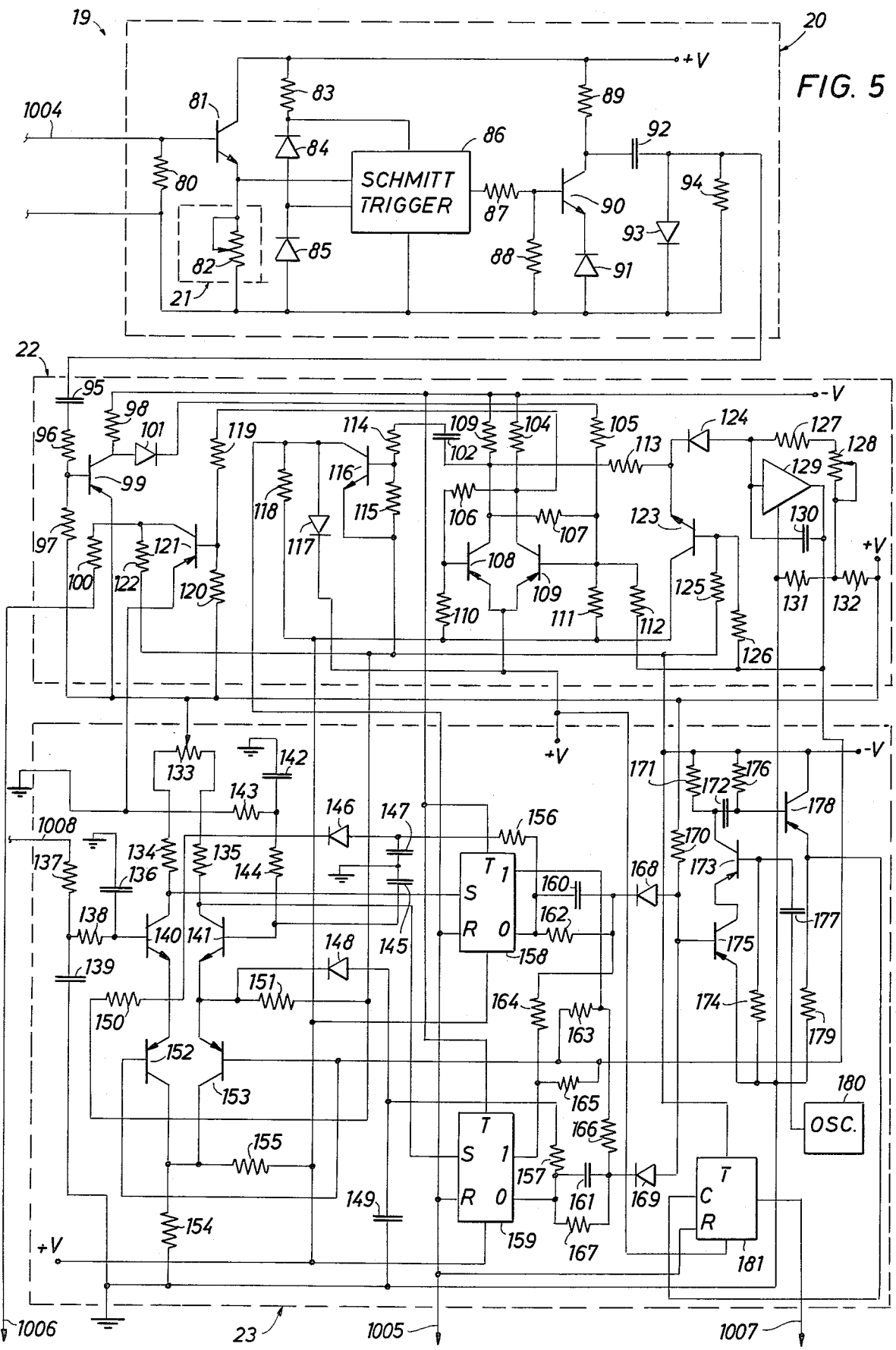
FIG. 5 is a detailed component schematic of the gating unit shown in FIG. 3.

Attention is directed to FIG. 5 of the drawings, which is a detailed point-to-point wiring schematic of the gating unit 19. It will be recalled that FIG. 3 discloses four components in block form. The four components comprise the gating unit. In FIG. 3 of the drawings, they are shown in complete detail to incorporate the illustrated equipment. A description of portions of the equipment is helpful.

The input signal received from the controller 12 is input to the clamp circuit 20. It is designed with an input transistor 81 which is an emitter follower circuit. The emitter follower circuit forms an output which is constrained in deflection by Zener diodes 84 and 85 which function with a Schmitt trigger 86. This limited signal is then input to a transistor 90. The output is a pulse which, in effect, reflects the clamped value. In other words, the output signal is clamped, and wide ranging variations are limited.

Operation of the circuit is controlled by manipulating the adjustable resistor connected to the emitter of the transistor 81.

The gating unit 19 functions in the following manner. After the resistor 21 has been set to determine a threshhold, the input signal is current amplified and applied to the trigger circuit. The trigger circuit forms an output level change when the input signal crosses a specified threshhold. When the crossing occurs, the change is reflected by forming a plateau or level output signal at the collector of the transistor 90. The transistor 90, however, is not connected directly to the output. A differentiating circuit is incorporated. Positive going differentiated pulses are grounded by the diode 93. The negative going portion of the signal is in the form of a negative going pulse is obtained by differentiation through the capacitor 92 and the grounded resistor 94, resulting in the formation of a negative going output pulse. This negative going pulse is the output of the circuit means 20 shown in FIG. 5. It is then input to the waveforming circuit 22.

The transistor 99 receives the input which is a negative pulse of relatively narrow duration. This is a trigger pulse which is applied through the diode 101 to the transistor pair 108 and 109. They are so connected that they function as a flip-flop. A reset circuit including the transistor 116 forms a reset pulse which is output from the transistor 116 connected to the reset terminal of the flip-flops 158 and 159 in the comparator circuit 23. In addition, an input pulse is applied to the amplifier 129. The operational amplifier 129 is connected with a feedback circuit comprising a capacitor 130. The capacitor 130, dependent on its size, functions as an integrating circuit. The output of the amplifier 129 is thus the integral of the signal which is input to it and is something in the form of a triangular waveform or ramp, and the ramp runs up to a point in time. Discharge, of course, restores it to a base line condition, and discharge occurs at a later time. In effect, a ramp or sawtooth waveform is created by the amplifier 129, and this is the input signal to the comparator circuit 23.

The amplifier 129 is input to the transistor pair 152 and 153. They share a common collector resistor. Accordingly, as current flow through one increases, the flow through the other decreases. It will be observed that the variations in current flow in the two transistors are reflected by changes in potential at the emitter connected transistors 140 and 141. A value is initially defined for the comparator circuit 23. As the ramp input to this circuit changes the current flow through the two legs comprising four transistors, a crossover must eventually be achieved. When this crossover occurs, it is sensed at the set input terminals of the flip-flops 158 and 159. These terminals are directly connected to the transistors 140 and 141. In other words, as the ramp voltage increases, it eventually equals a particular setpoint value. When it crosses this value, this is signalled through the set terminals of the flip-flops. The flip-flops were, theretofore, reset by the transistor 116 which formed the reset signal. This then enables the flip-flops to anticipate an input set signal. When this occurs, they reverse their states.

The flip-flops 158 and 159 are similarly connected at their outputs. They function in similar fashion to form output signals through the coupling diodes 168 and 169. An oscillator 180 forms an output signal which is gated off by the transistor 175. When that transistor is enabled, a pulse is received from the flip-flops connected to it; then it switches on. This then permits the transistor 173 to operate. As it operates, the oscillator signal having the form of a procession of pulses flows through the transistor 178 to form a saturated output. It is then output from the transistor 178 to a trigger circuit 181. The pulses are output from the trigger circuit to the memory unit 24. The duration of the pulses is, in part, determined by the signal input from the thermocouple amplifier 38. This input is to the base of the transistor 140. Accordingly, the number of pulses is dependent on that voltage and the rate of change of the ramp which is created by the circuit 22. Moreover, this has the form of a procession of pulses delivered to the memory unit 24. The procession of pulses delivered to the memory unit is stored. The number of pulses is stored at that device. It is stored until the next occurrence which, again, has the form of a successive procession of pulses. This repetitious cycle continues indefinitely. The process is repeated indefinitely. Very few controls are incorporated other than the potentiometers 82, 128 and 133. These adjust scale factors so that the device can be used with widely different circumstances.

Figure 11:
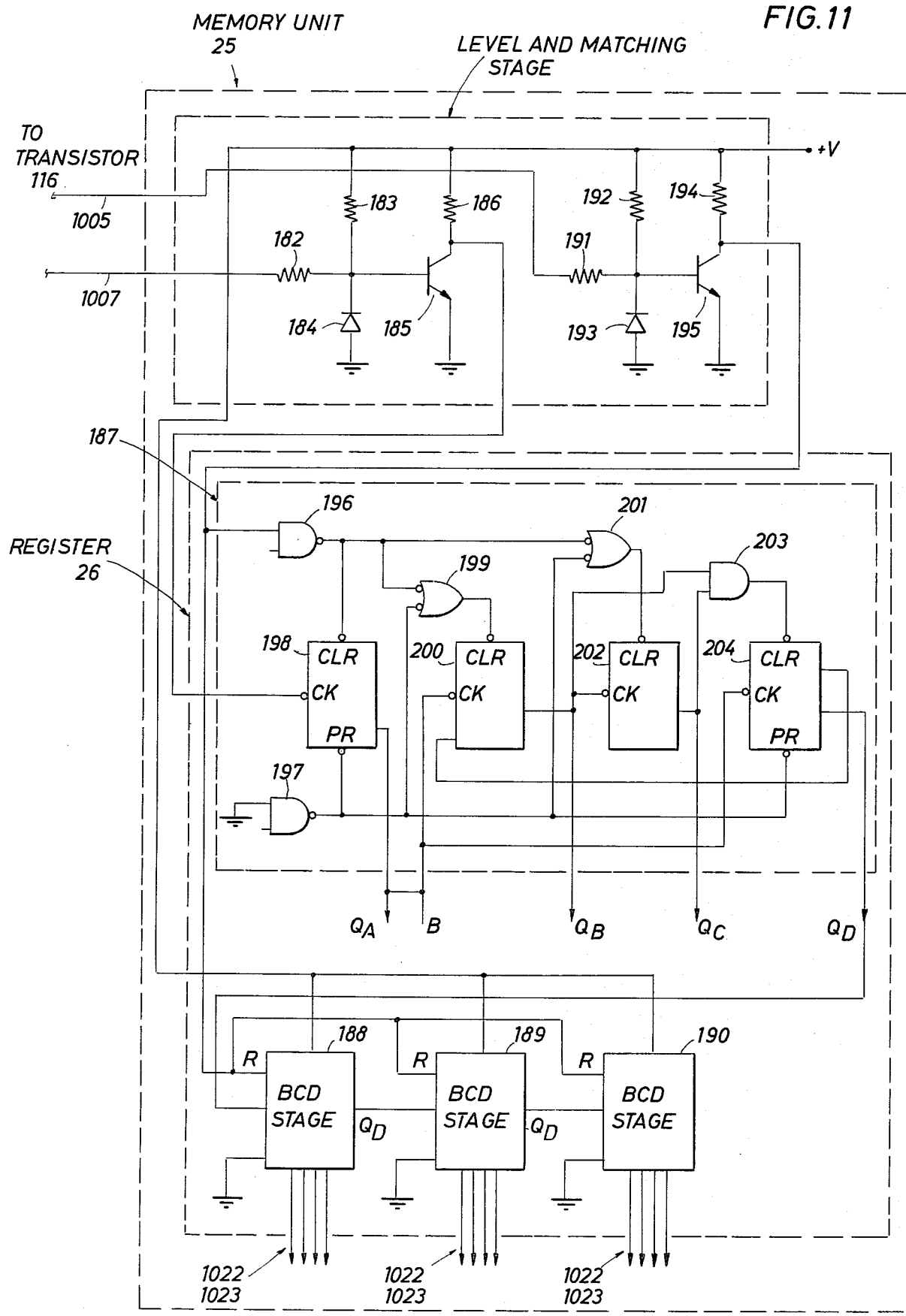
FIG. 11 is a detailed view of the apparatus shown in FIG. 10.

Attention is next directed to FIG. 11 of the drawings. It shows a detailed circuit schematic of the memory unit 24. Accordingly, FIG. 11 discloses these details. The transistor 116 just described forms a reset pulse which is applied to the transistor 195. The transistor 195 is a switch which gates off or on. A similar switch circuit is found at 185. It incorporates a transistor which is used in a switching mode, not as an amplifier. The two transistor circuits are thus provided with similar base control voltage circuits. They are provided with similar collector resistors, and they form output signals which are primarily dual valued. They are either switched off or on. They are either in saturation or substantially nonconductive. The remainder of FIG. 11 discloses digital pulse handling circuitry. There are several decade counters incorporated. One is shown in detailed circuit configuration at 187. The counters 188, 189 and 190 are shown in block diagram fashion. The counter 187 is identical to the others. A description of the first will suffice for the others.

The first counter 187 has a reset input terminal. It is connected to reset the entire circuit. The transistor 185 (a switching transistor) inputs the procession of pulses to the first of series of trigger circuits 198, 200, 202 and 204. The trigger circuits are connected in cascade fashion to count pulses in binary form but are wired so that they form a BCD output. The device functions in the following manner. First of all, it must be reset, and this is applied to the transistor 195, the gate 196 and additional gates 199, 201 and 203. This sets all of the trigger circuits to a zero state. The zero state is achieved in all four trigger circuits. A procession of pulses is delivered through the switching transistor 185. As they are delivered, they are counted. As an easy example, the first pulse is represented by a binary one in the first stage, or stage 198 of the cascaded trigger circuits. A second pulse causes another operation of the trigger 198 and transfer of a pulse to the next stage so that a binary one is stored at trigger circuit 200. This is repeated indefinitely until the circuit counts to nine. The ninth count or pulse is represented by the logical value of 1001 in the four trigger circuits. When the tenth pulse occurs, the storage element 187 recycles to zero and forms a carry pulse. This carry pulse is delivered to the integrated circuit 188 which is the second stage of the multidecade BCD storage device. It functions in the same manner.

After one hundred pulses have been received, the circuit 187 has formed sufficient carry pulses to completely cycle the storage element 188 through ten steps and thereby transfers a single pulse to the storage element 189.

As will be understood, the four storage elements have increasing significance so that the most significant digit is the storage element 190. As a consequence, thousands are stored at 190, while the storage element 189 indicates hundreds. The storage 188 stores tens, while units are stored at 187. As an easy example, the number may range anywhere from a small number upwards to 9999. Of course, this value is destroyed when a reset pulse is received.

At this point, a multidigit word is stored in memory. This word has a value which is proportionate to the controlled mode of operation. It is stored until the next recurrent word is formed which may be the same value or which may be different. The value stored in the register 26 is usable. It is proportionate to the dew point temperature.

Figure 7:
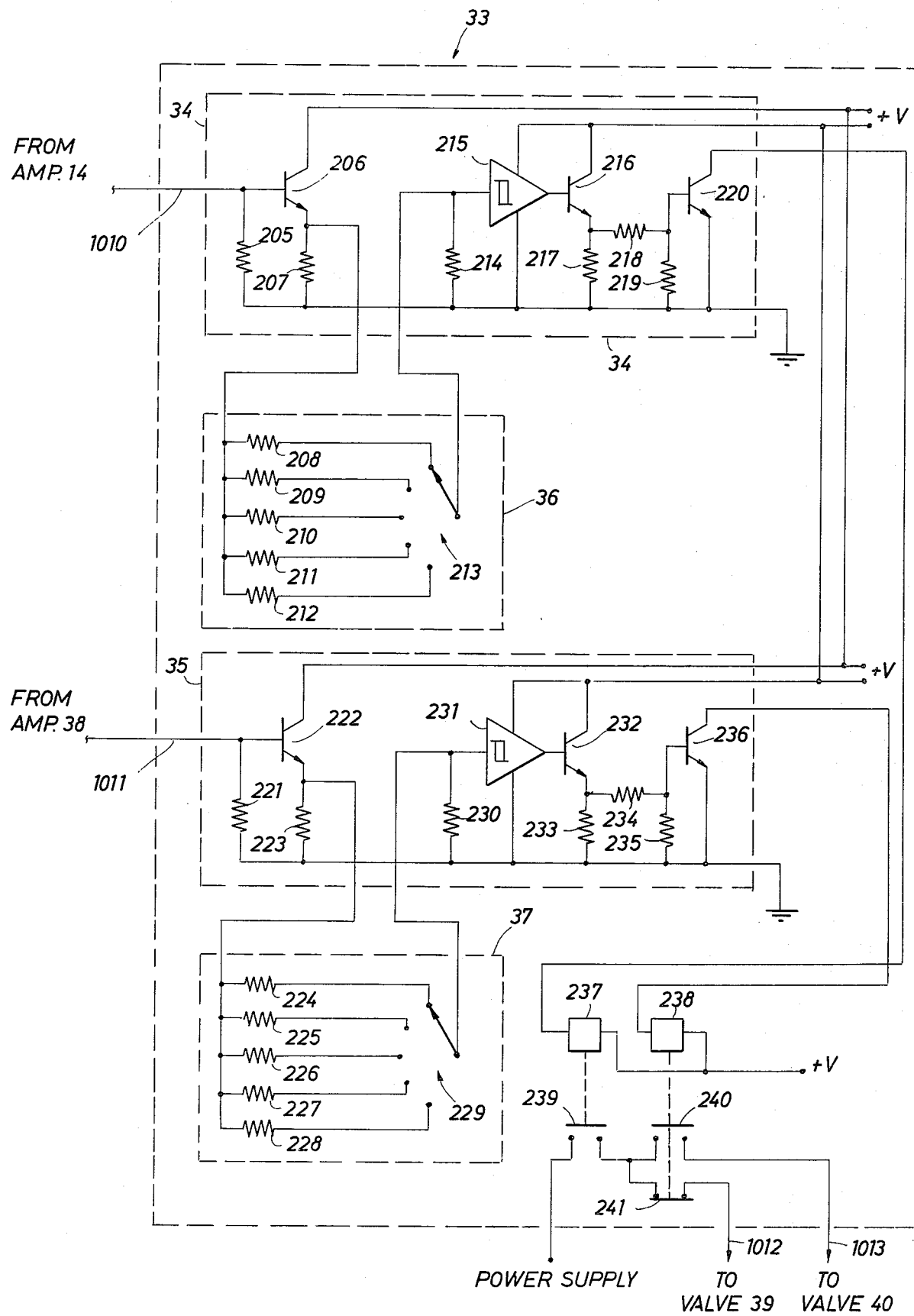
FIG. 7 is a detailed circuit diagram of the cooling speed control unit shown in FIG. 6.

Attention is next directed to FIG. 7 of the drawings for additional description. FIG. 7 is the cooling speed control unit. In essence, it functions in the manner set forth broadly in FIG. 1 whereby certain valves are opened and closed to control coolant flow. FIG. 7 is a control circuit for coolant flow. As will be observed on viewing FIG. 7, the valves 39 and 40 are controlled by suitable relays. The valves might be quite large in comparison with the signal current levels. The current levels which are formed in the circuit at FIG. 7 switch relays. In particular, the two relays are able to switch a higher voltage level for operation of the valves. It will be observed that the cooling speed control unit 33 incorporates a pair of amplifier circuits which are substantially identical in construction. The two circuits are both provided with initial setting controls at 36 and 37. They have the form of adjustable resistors which control the drop between stages of the amplifier circuits. The two amplifier circuits thus function in like manner to, dependent on adjustment, control the trigger level at which the relays are operated.

The device preferably utilizes Schmitt triggers. It will be understood that analog values are input to the two amplifiers. It is difficult to operate relays (binary functioning devices) dependent on analog values. These analog values are amplified at the first transistor stage and applied to an integrated circuit Schmitt trigger. The Schmitt trigger senses crossing of a threshhold value dependent on the setpoint and thereby forms a step function output. This is achieved in both of the circuits shown in FIG. 7. The step function output is sufficiently high to operate the relay. It will be understood that a Schmitt trigger maintains its output signal indefinitely, dependent solely on the input. As long as the input exceeds the specified threshhold value, the Schmitt trigger maintains the step function. When the input value drops below the threshhold, the Schmitt trigger drops from its plateau voltage, and the connected relay is switched.

It will be recalled that the exposed temperature transmitter includes electrodes 2 on the external surface. Flue gases form condensate on it. The condensate bridges the electrodes as a signal from the electrodes 2 to the power amplifier 14 and eventually to the cooling speed control unit 33. An operating level is set at the means 36. The Schmitt trigger is then conditioned for operation and achieves operation depending on the input voltage.

Figure 8:
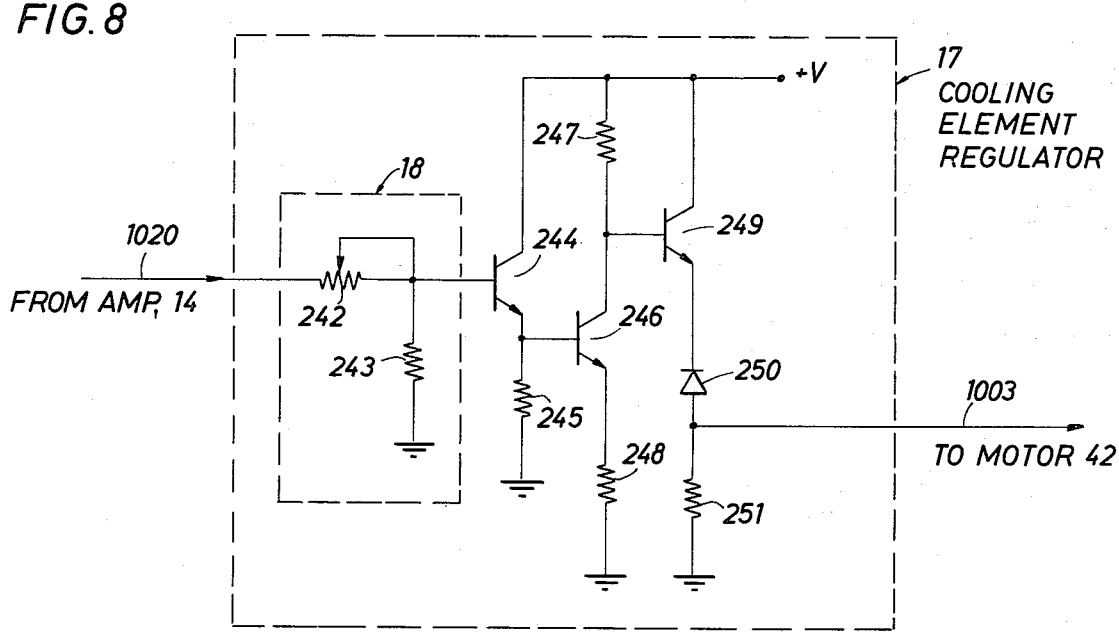
FIG. 8 is a detailed circuit diagram of the cooling regulator means.
Figure 9:
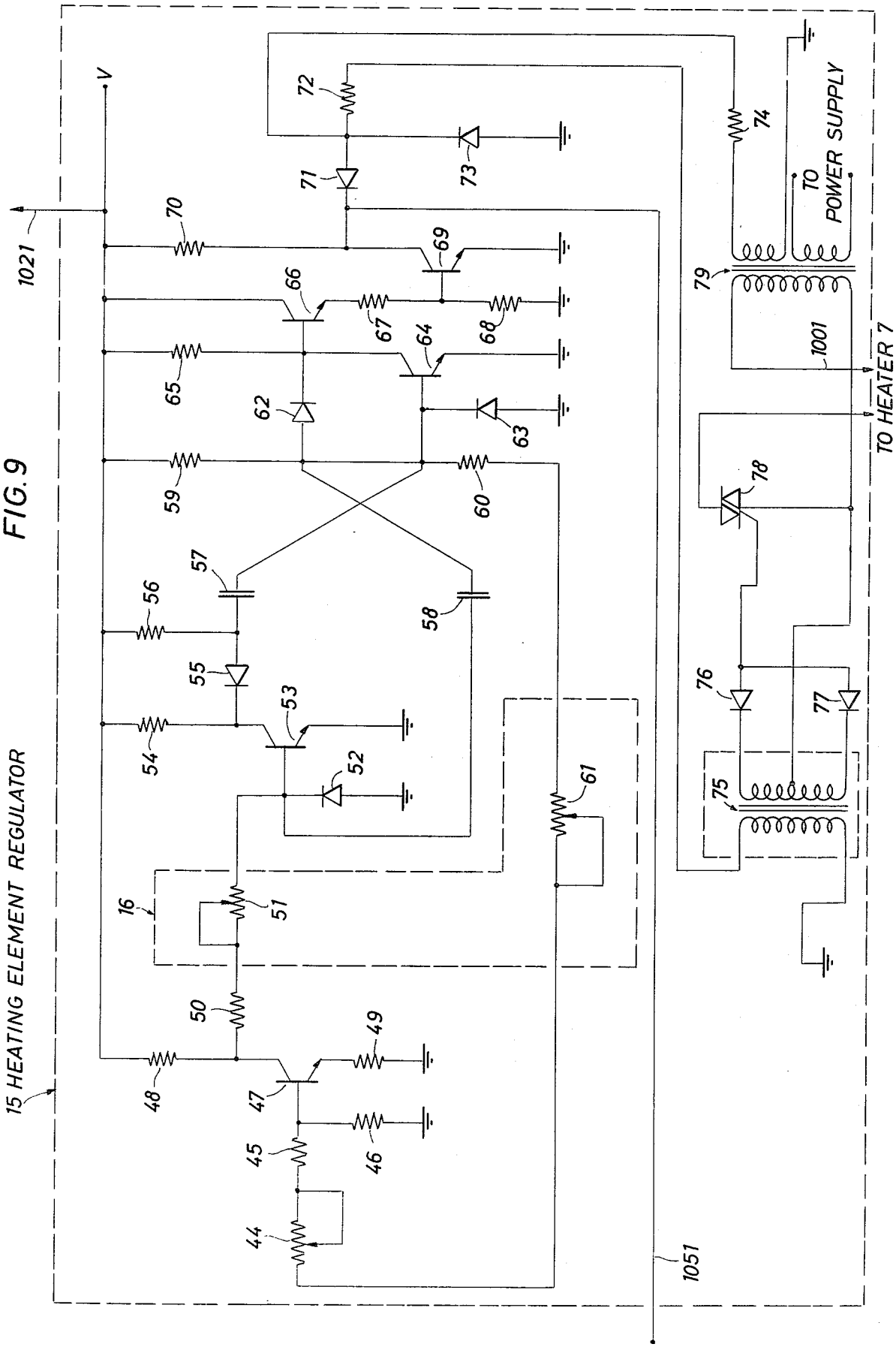
FIG. 9 is a detailed diagram of the heating element regulator means.

Attention is next directed to certain remaining components which have not been described in detail. Previously, a cooling regulator 17 was mentioned, and it has an adjustable setpoint at 18. This is better shown in FIG. 8 of the drawings. In particular, it will be observed that it utilizes an output circuit comprising an emitter circuit of a transistor with Zener diode to form a nicely stabilized output voltage. Moreover, the cooling regulator 17 is provided with the amplified signal from the electrodes 2 (see FIG. 2) to utilize cascaded emitter follower circuits to provide current amplified signals for operation of the cooling equipment. Conversely, FIG. 9 shows the heating regulator circuit. In FIG. 9, the setpoint is shown at 16, while the remainder of the circuitry is illustrated generally at 15. It comprises the setpoint control which, in conjunction with the signal from the amplifier 14, controls current flow through the heating coil 7. The heating coil 7 is quite large and requires a very substantial current flow. The signal from the amplifier 14 is a relatively small signal, by comparison. This small signal is input through an amplifier circuit, compared with a setpoint and is then applied to a transformer 75. The transformer 75 is connected to control a silicon controlled rectifier 78. This gates on or off a very large current flow which is delivered through the outlet conductors to the heater 7.

FIG. 12 is connected to the thermocouple amplifier 38. This circuitry is a heater limiter 31 and suitable setpoint apparatus 32 for it. As shown in FIG. 12, it receives an input from the thermocouple amplifier. This is responsive to the temperature directly achieved on the exposed surface in the flue gases. There are times, of course, when it is necessary to shut off the heating element. There are times when it is necessary to turn it on. When the signal from the electrodes exceeds a threshhold value, this is encoded to a specified level compared by the setpoint 33 and the Schmitt trigger shown in FIG. 12 to form an output signal for the controller 12. This signal is delivered to the controller 12 to turn the heating element regulator off or on as disclosed in FIG. 9.

To this juncture, the various units which are shown in FIG. 1 have been farily well described. There is no need to show detailed schematics of the thermocouple amplifier 38 or the other amplifiers 13 and 14. These amplifiers are shown in block form, and it is submitted that a person of average skill in the art can readily devise an amplifier to suit the purposes set forth herein. The amplifier 38, as an example, works with a signal in the range of zero to 1.0 volt from a typical thermocouple. It is a low voltage signal requiring fairly high input impedence. The terminals 2 are input to the preamplifier 13. Preferably, a small voltage across the terminals 2, forms a current flow which is amplified. The current flow is dependent on the moisture condensing between the terminals 2. As more moisture condenses, more current flow is carried. Accordingly, the preamplifier 13 is, in actuality, a current amplifier with a high input impedence.

To assist in the detailed description of the present invention included in this disclosure, the various conductors which extend from drawing to drawing are identified by numerals of 1000 or more to fully specify the interconnection of the various components which are shown in block form in FIG. 1. Perhaps some description of these would be helpful.

The conductor 1000 extends from the electrodes 2 to the controller 12, as shown in FIG. 1. This is shown better in FIG. 2 where the conductor 1000 is input to the preamplifier 13. The numeral 10001 extends from the heating element regulator in FIG. 2 to the heating coil 7 shown in FIG. 1. The conductor 1002 extends from the output of the power amplifier 15 to the gating unit 19, as shown both in FIG. 1 and FIG. 3. This supplies the amplified electrode signal to the clamp circuit 20 previously mentioned. The conductor 1003 extends from the cooling element regulator 17 in the controller 12 as shown in FIG. 1. In addition, the conductor 1003 is shown in FIGS. 2 and 8. The conductors 1020 and 1021 are both shown in FIG. 2 connected to the cooling element regulator 17 and the heating element regulator 15. These two conductors are shown in detailed schematics of FIGS. 8 and 9.

Another output of the power amplifier 14 is on the conductor 1010 which is an input signal to the amplifier system 34, better shown in FIG. 6. This conductor is also shown in FIG. 7 input to the cooling speed control unit 33. FIG. 7 additionally discloses the conductor 1011 input to a second similar amplifier system. It is derived from the thermocouple amplifier 38. Accordingly, the conductor 1011 is also shown in FIG. 1. The output of the cooling speed control unit is control signals for the valves 39 and 40, and, to this end, FIG. 7 additionally discloses the conductor 1012 connected to the valve 39 and the conductor 1013 connected to the valve 40. These conductors are shown in FIGS. 1 and 7. Attention is momentarily directed to FIG. 12 of the drawings, where the heater limiter 31 is illustrated in detail. It has an input conductor 1050 which also extends from the thermocouple amplifier 38. The output is the conductor 1051 which extends from the limiter 31 in FIG. 12 to the heating element regulator 15 shown in FIG. 2. This conductor is also shown in detail in FIG. 9 of the drawings.

Several additional conductors are shown in FIG. 3. The conductor 1008 is from the thermocouple amplifier 38 and is input to the comparator 23. FIG. 5 is a detailed schematic of the gating unit 19, and it, accordingly, shows the conductor 1008. The comparator 23 forms an output signal on the conductor 1007. That conductor is also shown in detail in FIG. 11. FIG. 3 further discloses the waveform encoder which has two outputs, being the conductors 1005 and 1006. These two conductors originate in FIG. 5. The conductor 1005 is the source of a reset pulse generated by the transistor 116 and delivered on the conductor 1005 for resetting the counter register 26.

The signal on the conductor 1006 is generated at the transistor 121 and supplied on the conductor 1006 to the digital printer 30 shown in FIG. 4.

FIGS. 4 and 10 disclose the output data register unit 27 and the memory unit 24. There, it will be observed that the conductors 1022 and 1023 deliver data between the register 26 which counts to form a BCD encoded word and the digital recorder 30.

Operation of the device should be considered. Assume, first of all, that the electrodes 2 are dry and that no condensate has been formed on the surface of the transmitter unit 1. If this occurs, it indicates that the device is too hot to collect condensation. The actual transmitter temperature is sensed by the thermocouple 3, and this temperature is relayed to the components which are connected to it. In particular, it is provided to the cooling speed control unit 33. This unit includes the adjustments provided at 36 and 37. These adjustments limit the rate of change permitted. The manner in which this limit is achieved can be better understood on viewing FIG. 7, where setpoint controls are found at 36 and 37. They are adjusted so that, in conjunction with the input signals to the duplicate Schmitt trigger circuits, they determine the point of opening and closing of relays to thereby vary and controllably open the valves 39 and 40 through signals applied by the conductors 1012 and 1013. In any case, continuing on with the description of operation, should the electrodes 2 sense that there is no moisture whatsoever collected on the surface, this indicates that the surface is maintained at an elevated temperature and must be cooled to initiate condensation.

The thermocouple amplifier 38 measures a temperature which is input to the gating unit 19. This unit converts the analog temperature measurement signal into a procession of digital pulses which are, in turn, stored for an interval and which describe a value proportionate to the temperature. This temperature at other times would be the dew point temperature, but, at this instant, it is too high to be the dew point temperature as indicated by the absence of moisture on the surface of the device. This temperature measurement is stored in the memory unit 24. It is stored in the ordinary operation of the device, but it is known that this value which is stored is not indicative of the correct dew point.

The valves are opened to deliver additional coolant to the system. Repetitive measurements are taken, and the valves are continually adjusted. Assume that the adjustment brings the device to the point where condensate begins to accumulate on the surface. Even the accumulation of a slight film is sensed by providing a conductive path between the electrodes 2 which indicates that the threshhold has been crossed, bringing the device closer to the dew point temperature. Once the threshhold has been crossed, indicative of the accumulation of some condensate, a signal is then formed on the conductors 1000 and supplied to the controller 2. This signal is amplified through the amplifiers 13 and 14. This signal is applied to the heating element regulator and the cooling element regulator. This signal is amplified by the various stages and, thus, indicates that the temperature then measured by the thermocouple 3 is approaching dew point temperature. The device operates repetitively to make additional measurements. From measurement to measurement, the amount of moisture might vary. If it does vary in a trend indicating an increase, there is an upper limit to condensation. Such variations are reflected by increased current flow permitted between the electrodes 2. All the while, the thermocouple 3 indicates the temperature measured on the surface. Needless to say, the surface temperature is varied by the condensation accumulated on the surface of the transmitter 1. It is varied by the heating or cooling of that surface from the interior and is reflected by the accumulation of condensation on the surface. Eventually, a value of dew point temperature is achieved and measured. This is achieved at a time of equilibrium or balance between the rate at which additional condensate is deposited on the surface and prior condensate is boiled off. In other words, a steady state condition is achieved. The steady state position presumes, for purposes of description only, that the flue gases do not radically change. The upshot of this is that the device settles in on the dew point temperature and maintains a measurement of it.

Should conditions in the boiler change and thereby change the dew point of the flue gases, the device is able to follow such changes. The changes in the flue gases will be reflected by the change in condensate on the surface. Either a decrease or increase will be experienced. Accordingly, the device will follow such changes including recordation of the surface temperatures measured by the thermocouple 3.

It will be observed that a feedback loop is included in the system. The feedback loop actually branches and has two loops, one for controlling of the heating system and the other for control of the cooling system. Considering these two as a single loop, the feedback path thus originates with the measured temperature and accumulated condensation variables, forms a tentative value of dew point temperature, adjusts the loop to achieve stabilized condensation on the surface and then records the temperature again. Intermediate data is meaningful to show how the device approaches the actual dew point measurement.

The dew point measurement is extremely valuable in proper operation of furnaces and boilers. Accordingly, the device of the present invention can be used in conjunction with large furnaces and boilers to vary the feed stock, including the delivery of oxygen for combustion. This can be achieved to reduce the discharge of pollutants to atmosphere and to also prolong the life of the equipment. As an easy example, should there be excessive condensation in the boiler and connected stacks, rusting in the flue discharge path might be initiated prematurely.

The foregoing is directed to the preferred embodiment of the present invention, but the scope is determined by the claims which follow.

We claim:

1. Apparatus for continuous temperature measurement of the dew point of flue gases which apparatus is adapted to be installed in a stream of flue gases and comprises:
    (a) a condensation surface means which is adapted to be installed in a flue gas stream which surface means forms a condensate on the exposed surface thereof dependent at least in part on its temperature and the gases flowing in the stream of flue gases;
    (b) sensor means operative at said condensation surface means for determining the presence or absence of condensate formed on said surface means;
    (c) heating means for said condensation surface means for supplying heat thereto for raising the temperature thereof;
    (d) cooling means for cooling said condensation surface means;
    (e) temperature sensing means for sensing the temperature of said condensation surface means;
    (f) control means connected to said sensor means wherein said sensor means provides a signal at least partly dependent on an increase or decrease in the condensate thereon for forming a control signal indicative of the increase and decrease in surface condensate;
    (g) comparator means for comparing the signal from said control means against a reference signal wherein the output thereof is a signal applied to said heating means and said cooling means for controlling the operation thereof to vary the temperature of said condensation surface means which variation in temperature alters the rate at which condensate is formed on said condensation surface means to achieve a controlled rate of change in condensate, and wherein the absence of change in condensate is indicative of the dew point in the flue gases flowing past said condensation surface means;
    (h) output means connected to said surface temperature sensing means for forming an output signal proportionate to the surface temperature detected by said surface temperature sensing means;
    (i) memory means connected to said output means for receiving and storing the output signal thereof proportionate to the surface temperature measured by said surface temperature sensing means; and
    (j) memory control means connected to said memory means and additionally connected to said comparator means which control means is operated by the comparison determined by said comparator means, and wherein said comparator means determines the occurrence of a balance in the formation of additional condensate on said condensation surface means and the loss of condensate which balance causes formation of a signal by said comparator means supplied to said memory control means for operation of said memory means to store and hold the signal proportionate to surface temperature as representative of the dew point temperature of the flue gases flowing past said condensation surface means.

2. The apparatus of claim 1 wherein said heating means is a helical coil resistance wire heating element positioned on the interior of a surrounding cylindrical housing is adapted to be installed in the path of flow of flue gases, and further wherein said helical coil has at least one turn and is located adjacent to the cylindrical housing such that heat from said helical coil heats said housing.

3. The apparatus of claim 2 wherein said cooling means includes an inlet and outlet connected to a flow path adjacent to said cylindrical housing for circulating a coolant fluid therealong.

4. The apparatus of claim 1 wherein said heating means comprises a multiturn helical coil; and wherein said condensation surface means incorporates a cylindrical housing which surrounds said helical coil, and said helical coil is made of a resistance heating wire element to generate heat for transfer to said cylindrical housing, and wherein said coil turns further define a multiturn flow path for said cooling means which flow path is connected with an inlet and outlet for delivering the flow of a coolant therealong and which flow path is adjacent to said cylindrical housing; and further wherein said heating element is connected to a variable current source to vary the current flowing therethrough and thereby vary the heat formed by said heating means; and further wherein said cooling means comprises a valve connected with a source and in series with the inlet of the flow path to deliver a variable flow of coolant fluid to thereby vary the temperature of said condensation surface means.

5. The apparatus of claim 4 further including a radially extending, mounting flange for securing said condensation surface means in a flow path of flue gases and wherein an auxiliary cooling means incorporating an auxiliary flow path with an inlet and outlet therefor cools said flange.

6. The apparatus of claim 1 wherein said cooling means comprises:

(a) an inlet valve adapted to be connected with a source of coolant fluid;

(b) an inlet means connected to said valve;

(c) a flow path connected to said inlet means and which is wound in helical turns on the interior of said condensation surface means and which contacts the interior of said surface means to cool said surface means;

(d) an outlet means for said flow for removing coolant flowing along said fluid path away from said condensation surface means; and (e) means including a heat exchanger for cooling the coolant fluid flowing in said cooling means.

7. The apparatus of claim 1 wherein said sensor means comprises a pair of spaced electrodes on the external surface of said condensation surface means which electrodes are electrically insulated from one another by said condensation surface means such that the only means of establishing a current flow path therebetween is the formation of condensate on said condensation surface means, and further wherein said pair of electrodes are connected to an amplifier circuit means for increasing the output signal therefrom.

8. The apparatus of claim 7 wherein said surface temperature sensing means includes a thermocouple placed on the exterior surface of said condensation surface means for detecting the temperature thereof.

9. The apparatus of claim 1 wherein said comparator means forms a pair of control signals, one for said heating means and the other for said cooling means, and wherein said heating means comprises a resistance wire heating element provided with electrical power from a power source and the quantity of power delivered from the power source is determined by a silicon controlled rectifier to vary the heat delivered by said heating means to said condensation surface means.

10. The apparatus of claim 9 wherein said comparator means additionally forms a control signal for said cooling means and said cooling means comprises a valve for selectively controlling the rate of flow of a coolant fluid to said condensation surface means.

11. The apparatus of claim 10 wherein said cooling means includes a valve having binary conditions which are off and on and the signal provided thereto gates the valve open or closed as required.

12. The apparatus of claim 1 wherein said memory means stores and holds the last recalled value of said output means which is a signal proportionate to the dew point temperature as sensed by said surface temperature sensing means, and further wherein said memory control means replaces and updates that value dependent on control from said comparator means which is, in turn, dependent on the determination of said control means.

13. The apparatus of claim 1 wherein said comparator means utilizes a procession of pulses from an oscillator source to a storage register wherein the number of pulses stored therein forms a data word, and the number of pulses in said data word is proportionate to the dew point temperature, and further wherein said memory means includes a storage register for receiving and storing a multibit, binary representation of the data word proportionate to dew point temperature.

14. The apparatus of claim 13 including means for resetting said storage register to zero and means for terminating counting therein of pulses from said oscillator source.

15. The apparatus of claim 14 further including a means recognizing the end of the operation wherein pulses are stored in said storage register and including a buffer means for transfer of a multibit binary word therefrom.

16. The apparatus of claim 1 wherein said surface temperature sensor means is connected to an amplifier means which forms an output signal and which output signal is then provided to said output means as an analog value and which analog value is utilized by said output means in conjunction with said comparator means to form a multibit digital word indicative of dew point temperature.

17. The apparatus of claim 16 including an oscillator for forming a procession of pulses connected to the input of a storage register; means for resetting said storage register to zero; means for inputting oscillator pulses thereto for a period of time which is variable to thereby vary the number of pulses stored in said storage register; and means for transferring the multibit digital word in said storage register therefrom and resetting said storage register to reinitiate the storage of pulses for a subsequent operation.

18. The apparatus of claim 1 including a heat conductive, current resistant, insulative material formed into a cylindrical housing and having an internal cavity therein which comprises said condensation surface means.

19. The apparatus of claim 18 wherein said heating means comprises a multiturn helical coil; and wherein said condensation surface means incorporates a cylindrical housing which surrounds said helical coil, and said helical coil is made of a resistance heating wire element to generate heat for transfer to said cylindrical housing, and wherein said coil turns further define a multiturn flow path for said cooling means which flow path is connected with an inlet and outlet for delivering the flow of a coolant therealong and which flow path is adjacent to said cylindrical housing; and further wherein said heating element is connected to a variable current source to vary the current flowing therethrough and thereby vary the heat formed by said heating means; and further wherein said cooling means comprises a valve connected with a source and in series with the inlet of the flow path to deliver a variable flow of coolant fluid to thereby vary the temperature of said condensation surface means.

* * * * *